(12) United States Patent
De Wael et al.

(10) Patent No.: US 11,614,423 B2
(45) Date of Patent: Mar. 28, 2023

(54) TRANSFORMED RESPONSE POTENTIOMETRIC TITRATIONS

(71) Applicant: UNIVERSITEIT ANTWERPEN, Antwerp (BE)

(72) Inventors: Karolien De Wael, Sint-Pauwels (BE); Luc Nagels, Heffen (BE); Guido Van Camp, Duffel (BE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 533 days.

(21) Appl. No.: 15/318,530

(22) PCT Filed: Jun. 14, 2015

(86) PCT No.: PCT/EP2015/063249
§ 371 (c)(1),
(2) Date: Dec. 13, 2016

(87) PCT Pub. No.: WO2015/189426
PCT Pub. Date: Dec. 17, 2015

(65) Prior Publication Data
US 2017/0122900 A1     May 4, 2017

(30) Foreign Application Priority Data
Jun. 13, 2014  (EP) .................................. 14172458

(51) Int. Cl.
*G01N 27/416* (2006.01)
*G01N 33/53* (2006.01)
*G01N 33/94* (2006.01)

(52) U.S. Cl.
CPC ......... *G01N 27/4161* (2013.01); *G01N 33/53* (2013.01); *G01N 33/946* (2013.01)

(58) Field of Classification Search
CPC ... G01N 33/53; G01N 33/946; G01N 27/4161
See application file for complete search history.

(56) References Cited

PUBLICATIONS

Matesic-Puac et al, Potentiometric determination of anionic surfactants using a new ion-pair-based all-solid-state surfactant sensitive electrode, Sensors and Actuators, 2005, vol. 106 pp. 221-228.*
Sekula et al, Coated Wire Potentiometric Detection for Capillary Electrophoresis Studied Using Organic Amines,Drugs, and Biogenic Amines, Analytical Chemistry, 2006, vol. 78, pp. 3772-3779.*
De Wael et al., "Use of Potentiometric Sensors to Study (Bio)molecular Interactions," Analytical Chemistry, Jun. 5, 2012, pp. 4921-4927, vol. 84, No. 11.
Durust et al., "Determination of DNA and its Binding to Protamine Using Potentiometric Polyion Sensors," Journal of Electroanalytical Chemistry, Mar. 8, 2007, pp. 138-141, vol. 602, No. 1.
Durust et al., "Potentiometric Determination of Some Food Additives and their Binding to a Polycationic Species Using Polyion Sensors," Turkish Journal of Chemistry, Apr. 17, 2013, pp. 308-315, vol. 37.
Ebel et al., "Fully Automatic Potentiometric Titrations," Angew. Chem. Int. ED. Engl., Mar. 1, 1977, pp. 157-169, vol. 16, No. 3.
Gran, "Determination of the Equivalence Point in Potentiometric Titrations. Part II," Section 3: Electrical Methods, International Congress on Analytical Chemistry, Nov. 1, 1952, pp. 661-671, vol. 77.
International Search Report for corresponding International PCT Application No. PCT/EP2015/063249, dated Sep. 7, 2015.
Meyerhoff et al. "Antibody Binding Measurements with Hapten-Selective Membrane Electrodes," Science, Feb. 4, 1977, pp. 494-495, vol. 195.
Scatchard, "The Attractions of Proteins for Small Molecules and Ions," Annals of the New York Academy of Sciences, Jan. 1, 1949, pp. 660-672.
Valsami et al.,"Complexation Studies of Cyclodextrins with Trycyclic Antidepressants Using Ion-Selective Electrodes," Pharmaceutical Research, Jan. 1, 1992, pp. 94-100, vol. 9, No. 1.
Zelada-Guillen et al., "Ultrasensitive and Real-Time Detection of Proteins in Blood Using a Potentiometric Carbon-Nanotube Aptasensor," Biosensors and Bioelectronics, Mar. 1, 2013, pp. 366-371, vol. 41.
Zellmer, "Gran's Plotting for End Point Detection," URL: http://zimmer.csufresno.edu/~ davidz/Chem102/GransPlot/GransPlot.html, downloaded Aug. 24, 2015, pp. 1-3.
Hilton et al., "A Microfluidic Affinity Sensor for the Detection of Cocaine", Sensors and Actuators A: Physical, vol. 166, 2011, pp. 241-246.

* cited by examiner

*Primary Examiner* — Bethany L Martin
(74) *Attorney, Agent, or Firm* — Workman Nydegger (57) ABSTRACT

The present invention relates to a method and system for obtaining an interaction property between a molecule or biomolecule or particle or bioparticle or nano- or microparticle on the one hand and a target particle on the other hand. The method comprises obtaining potentiometric titration results for a potentiometric measurement during titration of a solution with a titrant, said solution being a solution of one of a ligand of the target particle or said molecule or biomolecule or particle or bioparticle or nano- or microparticle. Said titrant comprises the other of said target particle ligand or said molecule or biomolecule or particle or bioparticle or nano- or microparticle. The method also comprises deriving based on said potentiometric titration results an interaction property between said molecule or biomolecule or particle or bioparticle or nano- or microparticle and said target particle.

9 Claims, 7 Drawing Sheets
Specification includes a Sequence Listing.

TRANSFORMED RESPONSE POTENTIOMETRIC TITRATIONS

FIELD OF THE INVENTION

The invention relates to the field of characterization of interactions between particles. More particularly, the present invention relates to methods and systems for characterizing interaction between molecules based on potentiometric titration.

REFERENCE TO SEQUENCE LISTING SUBMITTED VIA EFS-WEB

This application includes an electronically submitted sequence listing in .txt format. The .txt file contains a sequence listing entitled "19828-189-Sequence_Listing_ST25.txt" created on Aug. 5, 2022 and is 957 bytes in size. The sequence listing contained in this .txt file is part of the specification and is hereby incorporated by reference herein in its entirety.

BACKGROUND OF THE INVENTION

A myriad of label free methods exist to obtain quantitative information on the affinity between two different (bio) molecules or between (bio)molecules and small molecules, or between particles (nano-, micro-, bioparticles . . . ) and molecules. These include (but are not restricted to) surface plasmon resonance (SPR), isothermal- and differential scanning calorimetry (ISC, DSC), quartz microbalance (QMB), evanescent wave sensors, affinity chromatography, and circular dichroism (CD). Studying molecular interactions is a vast area of research in many biological, biomedical, and analytical processes such as cell signaling pathways, proteomic analysis, antibody development, drug discovery, biosensors etc.. The market for biosensors is expected to grow rapidly, especially in point of care diagnostics, home diagnostics, and environmental areas. Measuring the interaction characteristics of a biomolecule, used as a receptor in a biosensor, is therefore one of the many potential areas of application. Biomolecules such as aptamers and antibodies are very promising elements in such biosensor constructions, as they selectively interact with the targeted analyte. Yet, still very little is known on the selectivity of aptamers and antibodies, especially if they were selected to recognize small (organic) molecules.

Also quite unknown is the comparison of association constants $K_a$ (or its inverse, $K_d$) of e.g. aptamer/analyte interactions to $K_a$ values of receptor molecules/analyte combinations which are also used abundantly. This is especially true for potentiometric sensors. One of the important successes of potentiometric techniques was achieved with a biomolecule (valinomycin) as a recognition element, around 1970. As already shown as early as 1974 for this valinomycin receptor molecule, the selectivity and sensitivity depend strongly on $K_a$ values, which were determined with circular dichroism titrations. The performance of this field of electrochemistry has dramatically improved. In a later stage, many attempts were noted for the renewed use of biomolecular recognition elements, and for the determination of biomolecular analyte targets.

Most of the techniques mentioned above for studying molecular, e.g. biomolecular, interactions are expensive, time consuming and complicated. They can quantify the affinity from concentration based assays, or by measuring the kinetics of association and dissociation. In the concentration based assays, the formation of a molecule/small molecule complex is studied with binding curves. These are titration curves where the ligand is added as a titrant to a solution of the biomolecule, and the extent of formation of the complex is plot on the y-axis. A potentiometric sensor doped with biomolecules for the determination of small molecule/biomolecule interactions via binding kinetics was already reported.

SUMMARY OF THE INVENTION

It is an object of embodiments of the present invention to provide good methods for characterizing interactions between molecules.

It is an advantage of embodiments of the present invention that a practical method for determining bioreceptor/analyte interactions is provided. It is an advantage that, by using biomolecular recognition elements, potentiometric sensing devices can be provided allowing accurate detection.

It is an advantage of embodiments of the present invention that a simple and general potentiometric method can be provided for determining interaction properties between molecules.

It is an advantage of embodiments of the present invention that a non-expensive method for determining interaction properties between molecules can be provided.

It is an advantage of embodiments of the present invention that a label-free potentiometric method for the determination of interaction properties between molecules can be provided.

It is an advantage of embodiments of the present invention that these can be used in fast bio-recognition platforms, not only for biosensors but also for molecular biology, biomedicine, and pharmacy.

The above objective is accomplished by a method and device according to the present invention.

The present invention relates to a method for obtaining an interaction property between a molecule or biomolecule or particle or bioparticle or nano- or microparticle on the one hand and a target particle on the other hand, the method comprising obtaining potentiometric titration results for a potentiometric measurement during titration of a solution with a titrant, said solution being a solution of one of a ligand of the target particle on the one hand or a molecule or biomolecule or particle or bioparticle or nano- or microparticle on the other hand and said titrant comprising the other of said target particle ligand or said molecule or biomolecule or particle or bioparticle or nano- or microparticle, and deriving based on said potentiometric titration results an interaction property between the a molecule or biomolecule or particle or bioparticle or nano- or microparticle on the one hand and the target particle on the other hand.

In some particular embodiments, said solution comprises said target particle ligand and said titrant comprises said a molecule or biomolecule or particle or bioparticle or nano- or microparticle.

Said potentiometric measurement may be performed using a potentiometric indicator electrode and a reference electrode.

Obtaining potentiometric titration results may comprise obtaining the potential of the potentiometric indicator electrode in relation to the added titrant volume.

The titration results may be obtained using an ion-selective potentiometric electrode.

The method may comprise transforming the obtained potentials to a concentration related signal and wherein said deriving comprises deriving an interaction property based on said concentration related signal.

The transformation may comprise replacing the potential (mV) signal of a potentiometric sensor by a transformed response, which is linearly related to the ligand concentration. This may be done also in the region where the sensor's calibration curve deviates from linearity, i.e. one decade of molar concentration above the LOD (limit of detection) as defined uniquely in potentiometry.

It is an advantage of embodiments of the present invention that a simple transformation can be applied which is generally applicable in potentiometry.

It is an advantage of embodiments of the present invention that the methods can be applied for example, but not limited to cocaine as a ligand, other positively charged organic ligands, especially when their log P value is not extremely low (e.g. log P>1), negatively charged ligands (using sensors with anion responsivity) etc. Other examples are pharmaceuticals, and biochemically important molecules, but also food components, detergents, pesticides, and many industrially important chemicals belong to this class. Also the target molecule or biomolecule or particle or bioparticle or nano- or microparticle encompasses a wide range of substances such as large biomolecules (Molecular weight>1000, proteins, DNA, RNA, aptamers, antibodies . . . ), organic and inorganic nano- and microparticles, colloids, suspended particles, bioparticles (bacteria, viruses, cells, and parts of such biomaterials).

Said transforming may be performed over a concentration interval including concentrations where the relation between the obtained potential and the logarithm of the concentration of the target particle is not linear.

Most potentiometric calibration curves (potential on the y-axis, and logarithm of molar concentration on the x-axis) deviate from linearity at molar concentration values which are lower than one decade above the LOD (Limit of Detection, as defined uniquely in potentiometry). In the best cases, this is at concentration values lower than $10^{-5}$ M, but often this is already the case below $10^{-4}$ M and even at $10^{-3}$ M concentrations.

Said transforming may take into account the following equation:

$$tR \propto 10^{E/S} - 1$$

wherein tR is the transformed response, E is the obtained potential and S corresponds with (RT/zF) with zF the charge per mole of analyte present in the potential-forming process, R the molar gas constant and T the Kelvin temperature.

The potentiometric titration results may be obtained at the equivalence point of the potentiometric titration. The accuracy for the determination of the association constant $K_a$ is directly related towards the accuracy for the determination of the equivalence point. The latter is often obtained via the well-known first derivative method.

In difficult cases (with few measuring data), the equivalence point may be obtained using the Gran method (see e.g., David L. Zellmer (Mar. 2, 1997). Gran's plot for end point detection. Retrieved from http://zimmer.csufresno.edu/~davidz/Chem102/GransPlot.html.

If the equivalence point is difficult to localize, the potentiometric titration results may be obtained beyond the equivalence point. The latter method is very practical.

The target particle may be a small molecule.

Said interaction property may be any of the binding strength or association constant $K_a$, the dissociation constant $K_d$ or the Gibbs free energy $\Delta G$ of interaction between the a molecule or biomolecule or particle or bioparticle or nano- or microparticle on the one hand and the target particle on the other hand.

The present invention also relates to a system for obtaining an interaction property between a molecule or biomolecule or particle or bioparticle or nano- or microparticle on the one hand and a target particle on the other hand, the system being adapted for performing a method as described above.

The present invention also relates to a system for obtaining an interaction property between a molecule or biomolecule or particle or bioparticle or nano- or microparticle on the one hand and a target particle on the other hand, the system comprising
an input means for obtaining potentiometric titration results for a potentiometric measurement during titration of a solution with a titrant, said solution being a solution of one of a ligand of the target particle or said a molecule or biomolecule or particle or bioparticle or nano- or microparticle and said titrant comprising the other of said target particle ligand or said a molecule or biomolecule or particle or bioparticle or nano- or microparticle, and
a processing means for deriving based on said potentiometric titration results an interaction property between said molecule or biomolecule or particle or bioparticle or nano- or microparticle on the one hand and the target particle on the other hand.

The processing means may be programmed for transforming the obtained potential to a concentration related signal and for deriving an interaction property based on said concentration related signal.

The transformed data may also cover the lower concentration range around and below the limit of detection (LOD). Typical LOD values in potentiometry are around $10^{-6}$M. One can go easily 10× below the LOD value, also if the latter is lower than $10^{-6}$M. Limits of detection are defined totally differently in potentiometry as compared to other analytical techniques, and there is actually no objection to work accurately beyond these artificial LOD values.

The transformation may take into account that potentiometric calibration curves (mV versus log $C_{analyte}$ plots) are not linear in that low concentration range.

It is an advantage of embodiments of the present invention that potentiometric titration can be used in concentration ranges for molecular biology applications.

The processing means may be programmed for transforming over a concentration interval including concentrations where the relation between the obtained potential and the logarithm of the concentration of the target particle is not linear.

The input means may comprise a controller for controlling a potentiometric titration and wherein the input means furthermore comprises a data receiver for obtaining the potentiometric titration results.

The present invention also relates to a sensor, e.g. a biosensor, comprising a system as described above.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to the equivalence point or stoichiometric point of a chemical reaction reference is made to the point at which an added titrant is stoichiometrically equal to the number of moles of substance (known as analyte) present in the sample: the smallest amount of titrant that is sufficient to fully neutralize or react with the analyte. In some cases there are multiple equivalence points, which are multiples of the first equivalence point. Where reference is made to measurement beyond the equivalence point, reference is made to measurements performed at a point where more titrant has been added than at the (first) equivalent point.

Where in embodiments of the present invention reference is made to a molecule or biomolecule or particle or bioparticle or nano- or microparticle, reference is made to a small molecule, a biomolecule, a dna or rna molecule, a virus, a bacterium, an organic or inorganic nanoparticle or microparticle, a bioparticle etc. Where in embodiments of the present invention reference is made to a target particle, reference may be made to another small molecule, a complex small molecule, large molecules, biomolecules, proteins, dna or rna, (bio)particles etc. With "small molecule" reference may be made to a molecule having a molecular weight lower than 1000.

Figure 1:
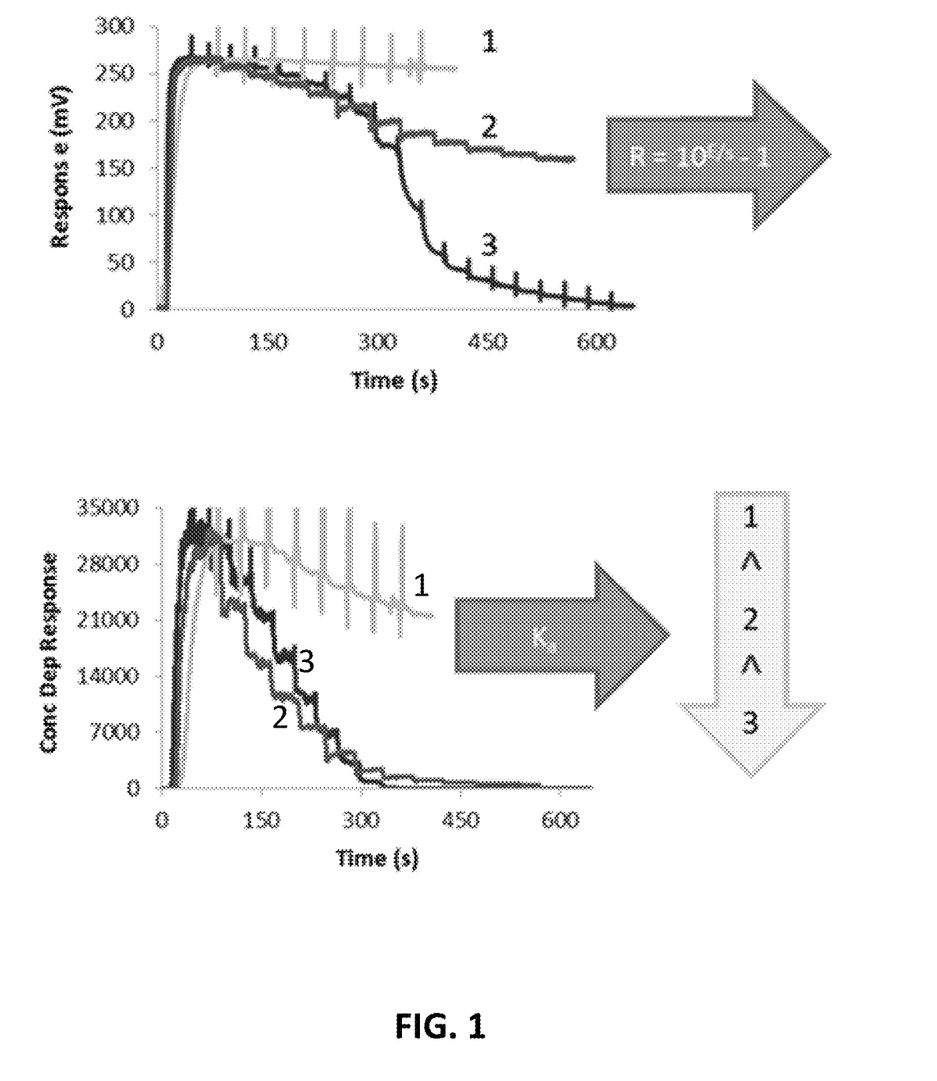
FIG. 1 shows a schematic representation of a method according to an embodiment of the present invention.

According to a first aspect, the present invention relates to a method for obtaining an interaction property between a molecule or biomolecule or particle or bioparticle or nano- or microparticle on the one hand and a target particle on the other hand. Such an interaction property may for example be a dissociation constant for the interaction between the bioparticle and the target particle, a binding strength between the bioparticle and the target particle or a Gibbs free energy for the interaction between the bioparticle and the target particle. The method comprises obtaining potentiometric titration results for a potentiometric measurement during titration of a solution with a titrant, said solution being a solution of one of a ligand of the target particle or said a molecule or biomolecule or particle or bioparticle or nano- or microparticle and said titrant comprising the other of said target particle ligand or said molecule or biomolecule or particle or bioparticle or nano- or microparticle. Obtaining potentiometric titration results may be receiving the data of the potentiometric titration results (typically a voltage signal as function of the amount of titrant added) as data input through a data transmission line (wired or wireless) or retrieving it from a memory. The data may be previously recorded. Alternatively, obtaining potentiometric titration results may include performing potentiometric titration and gathering the results for use. The method also includes deriving, based on said potentiometric titration results, the interaction property between the molecule or biomolecule or particle or bioparticle or nano- or microparticle on the one hand and the target particle on the other hand. According to at least some embodiments of the present invention such deriving may include first transforming obtained potential data to concentration related data and deriving the interaction property based thereon. Further features and advantages may be as described in the example and/or as described above. FIG. 1 illustrates an example of the different results obtained during implementation of a method as described above.

Figure 2:
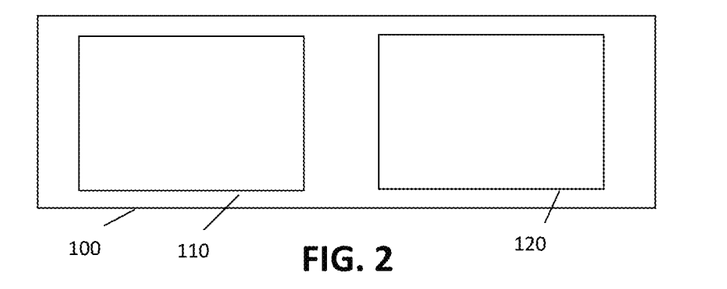
FIG. 2 shows a schematic block diagram of an exemplary system according to embodiments of the present invention.

According to a second aspect, the present invention relates to a system for obtaining an interaction property between a molecule or biomolecule or particle or bioparticle or nano- or microparticle on the one hand and a target particle on the other hand. Such a system may comprise an input means for obtaining potentiometric titration results for a potentiometric measurement during titration of a solution with a titrant, said solution being a solution of one of a ligand of the target particle or said (bio)molecule or (bio) particle or nano- or microparticle and said titrant comprising the other of said target particle ligand or said (bio)molecule or (bio)particle or nano- or microparticle. The input means may be a data receiving means for obtaining data, e.g. through a dataline, or it may comprise a potentiometric titration measurement system, a controller for controlling such a system, or alike, whereby the results obtained through measurement using the measurement system or controller are provided as data to receive. The system also comprises a processing means for deriving based on said potentiometric titration results an interaction property between the molecule or biomolecule or particle or bioparticle or nano- or microparticle on the one hand and the target particle on the other hand. Such a processing means may be any suitable processing means, such as a microprocessor, a CPU, etc. This may be programmed for performing a number of calculations for deriving based on the potentiometric titration results an interaction property. According to some embodiments, the processing means may be programmed for first transforming obtained potential data to concentration related data and deriving the interaction property based thereon. Further features and advantages may be as described in the example and/or as described above. The system may be especially suitable for performing a method as described in the first aspect. FIG. 2 illustrates a schematic representation of a system for obtaining an interaction property between a molecule or biomolecule or particle or bioparticle or nano- or microparticle on the one hand and a target particle on the other hand. The system 100 comprises an input means 110 for obtaining potentiometric titration results, a processor 120 or processing means for deriving based on the potentiometric titration results an interaction property between said molecule or biomolecule or particle or bioparticle or nano- or microparticle and said target particle.

EXAMPLE

By way of illustration, embodiments of the present invention not being limited thereto, an example illustrating standard and optional features of embodiments of the present invention is discussed below.

In the example, the utility of a special potentiometric titration approach for recognition and calculation of bioparticle/small molecule interactions is illustrated. The potentiometric titration measurement is based on the use of a classical polymeric membrane indicator electrode in a solution of the small molecule ligand. The bioparticle is used as a titrant. The potential is measured versus a reference electrode and transformed to a concentration related signal over the entire concentration interval, also at low concentrations, where the mV (y-axis) versus log $c_{analyte}$ (x-axis) function is not linear. In the specific example, the association constant value $K_a$ is calculated for the interaction of cocaine with a cocaine binding aptamer and with an anti-cocaine antibody. To study the selectivity and cross-reactivity, other oligonucleotides are tested, as well as other small ligand molecules such as tetrakis (4-chlorophenyl)borate, metergoline, lidocaine, and bromhexine. The calculated $K_a$ compares favorably to the value reported in the literature using SPR. The newly presented potentiometric titration method (called "Transformed Response Potentiometry"), makes it possible to determine $K_a$ for a large variety of macromolecular target particles and small molecule ligands.

Experimental

Chemicals

All the chemicals were of analytical reagent grade. 2-(N-morpholino)ethanesulfonic acid (MES) hydrate and high-molecular mass polyvinylchloride (PVC) was purchased from Acros Organics (Geel, Belgium). The other membrane components such as tetrakis chlorophenyl borate (TCPB), methyltridodecylammoniumchloride (MTDDAC1), 2-nitrophenyloctylether (NPOE) and tetrahydrofuran (THF) as solvent for the membrane's components were of the highest quality and from Fluka (Bornem, Belgium). Metergoline, lidocaine, cocaine and bromhexine were obtained from Sigma-Aldrich (Bornem, Belgium). Anti-cocaine antibody was purchased from Abcam (Cambridge, England).

The sequence of different oligonucleotides that were used in this research are as shown below:
  Cocaine Binding Aptamer (CBA), the sequence of which is shown in SEQ ID NO: 1;
  Non-specific oligonucleotide, the sequence of which is shown in SEQ ID NO: 2;
  43 mer Random Primer (43-mer-RP);
  Chloramphenicol Binding Aptamer (CAPBA), the sequence of which is shown in SEQ ID NO: 3.

The 25-mer-DNA and random primers were obtained from Integrated DNA Technologies (IDT, Gent, Belgium) and the others from Eurogentec (Liége, Belgium).

Instrumentation

Potentiometric Working Electrodes

The indicator electrode was made of a PVC cylinder (5 mm OD×40 mm length). It contained a cylindrical substrate electrode (3 mm diameter×1 mm length), which is an electronically conducting graphite/PVC composite material. The composite substrate electrode was polished with Carbimet grit 600 (Buehler Ltd, USA). The rubber phase sensing membrane was coated on the composite substrate electrode. The electrodes with a composite substrate had the important property that the coated membrane and the composite were tightly mixed at the interface.

The membrane coating used for the detection of positively charged analytes contained 2% (w/w) TCPB, 33% (w/w) PVC and 65% (w/w) NPOE. 100 mg of this mixture was dissolved in 1 mL THF and 2×40 μL of this solution were applied on the electrode surface (dip-coating) by 2 sequential steps. After evaporation at room temperature (1 h) the resulting ionically conductive rubber polymeric phase coated membrane had a thickness of 100 μm. The electrodes were kept in buffer solution (1 mM MES pH 7.0) for at least 3 h to obtain a stable baseline for the potentiometric titration. A membrane coating used for the detection of negatively charged analytes can optionally be used, containing 2% (w/w) MTDDAC1, 33% (w/w) PVC and 65% (w/w) NPOE.

Potentiometric Setup

The potentiometric titrations were performed using an indicator electrode and a reference electrode, in a 10 mm diameter beaker. The buffer solution (1 mM MES pH 7.0) was stirred during the entire experiment with a magnetic stirrer (5×2 mm). After obtaining a stable baseline, the first injection was done by addition of the analyte (5 μL) to 500 μL of the buffer solution. Always, an increase in potential could be seen in this step. After obtaining a stable signal, the titrant was added using a micropipette at constant time intervals. The usual volume of the titrant was 8 μL and pipetting was done every 30 s, unless otherwise stated. The membrane potential was measured against a homemade miniaturized (1.4 mm OD×40 mm length) reference electrode (Ag/AgCl) using a high impedance ($10^{13}\Omega$) homemade amplifier. The detection signals were recorded on a data station composed of a PC equipped with a 6013 NI DA converter and LabVIEW 7 (National Instruments, US) based software. The overall time constant of the high impedance amplifier plus data station was set to 200 ms. All the measurements were done at least three times on three different working electrodes after conditioning and stabilization in the MES buffer solution.

Results and Discussion

Potentiometric Detection of Cocaine in Batch System

Figure 3A:
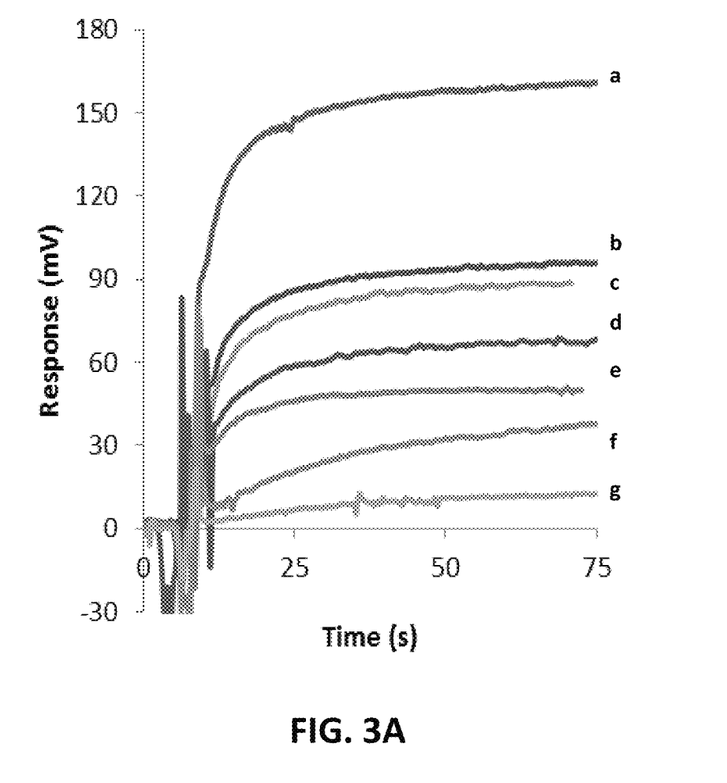
FIG. 3A illustrates typical potentiometric recordings in batch after cocaine injection, according to embodiments of the present invention, wherein the concentration of cocaine varied from $10^{-4}$ M (curve a) to $10^{-4.5}$ M (b), $10^{-5}$ M (c), $10^{-5.5}$ M (d), $10^{-6}$ M (e), $10^{-6.5}$ M (f) and $10^{-7}$ M (g) in 1 mM MES buffer (pH: 7.0).

FIG. 3A shows the potentiometric signal obtained after injecting different concentrations of cocaine in the batch system.

The potentiometric indicator electrode used was of the coated wire type, containing TCPB as an ionophore. Some initial spiking phenomena are observed (FIG. 3A) as we inject in a miniaturized (500 μL) system. The signal heights at the plateau values plotted versus the logarithm of the analyte concentrations follow calibration curves of the type expressed by Eqn. 1:

$$E = E^0 + S \text{Log}(c_{analyte} + Cst) \qquad \text{Eqn. 1}$$

Figure 3B:
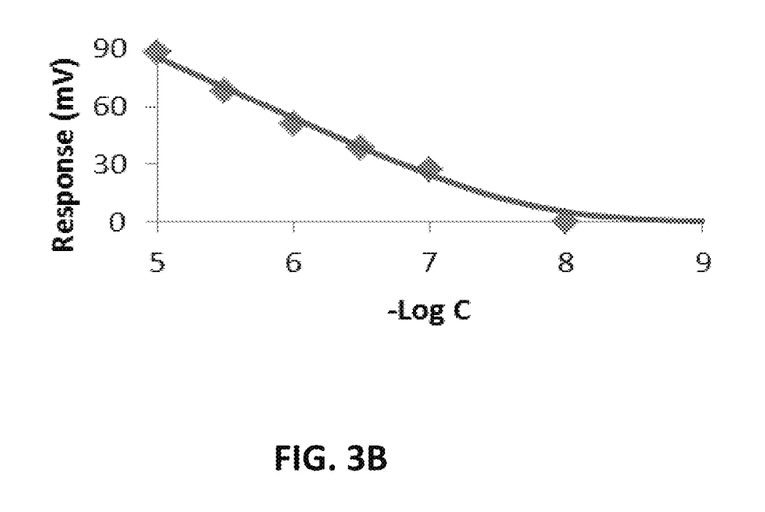
FIG. 3B shows potentiometric responses of $10^{-5}$ to $10^{-7}$ M cocaine injections (plateau values from FIG. 3A) in relation to log concentration. The measured potentiometric responses in FIG. 3A ($\diamond$)-fitted by "Solver" (curve) are shown.

This function has the typical form shown in FIG. 3B. Analogous calibration curve equations were used and discussed by other authors. This function has also been extensively used in analytical applications of these potentiometric sensors. E values (mV) are the responses at the plateau values in the potentiograms for each analyte concentration (FIG. 3A). $E^0$ is the value of the potential, obtained by extrapolating the analyte concentration, $c_{analyte}$, to a concentration of 1 M. S is the slope (RT/zF) of the calibration curve (FIG. 3B), in the linear part. zF is the charge per mole of analyte present in the potential-forming process, here 1 faraday. Cst is a constant, which depends on the degree of interference which is provoked by the buffer solution. It is equal to the limit of detection (LOD) as it is usually (and typically) defined in potentiometry. The 3 variables $E^0$, S and LOD are related:

$$LOD = 10^{-\frac{E^0}{S}}.$$

The equation for the calibration function as exemplified by FIG. 3B and Eqn.1 was obtained for cocaine in the conditions of FIG. 3B, by curve fitting via "Solver" (Microsoft Excel 2007) as $E=353+50.4$ [Log ($c_{analyte}$)$+98.3\times 10^{-9}$]. The obtained slope (S=50.4 mV) is used to convert the potentiometric response (in mV) to a concentration dependent response by equation 2:

$$c_{analyte} = (10^{E/S} - 1) \times LOD \qquad \text{Eqn. 2}$$

Figure 3C:
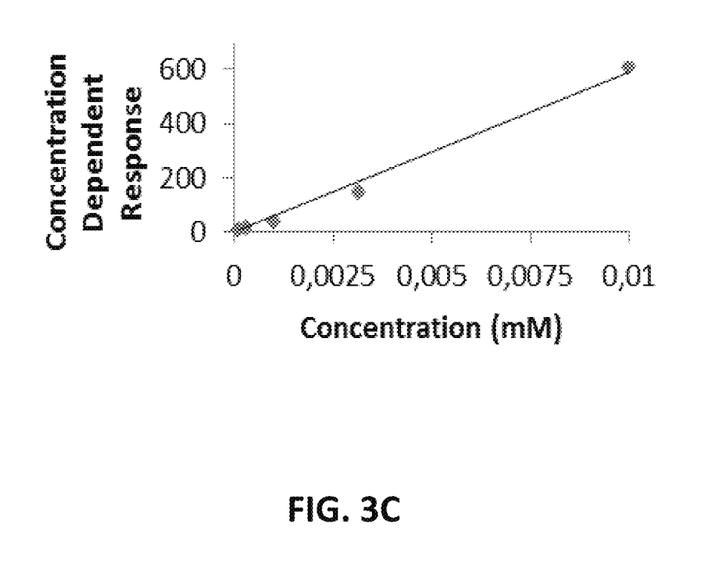
FIG. 3C shows potentiometric responses of $10^{-5}$ to $10^{-7}$ M cocaine injections after transformation of the y-axis to a concentration related signal as can be obtained using a method according to an embodiment of the present invention (see equation $tR \propto 10^{EIS}-1$ above).

The mV signal of the potentiometric sensor was transformed to $c_{analyte}$. In the present example this is performed by Equation 2 being the transpose of equation 1. The latter is illustrated in FIG. 3C. It is valid when E (eqn. 1) is set to zero for $c_{analyte}=0$. In practice, this is simply done by offsetting the output voltage (the baseline) of the high impedance voltmeter to zero for $c_{analyte}=0$ (i.e. when measuring or recording in pure buffer solution). Or by offsetting the recorded data to a zero baseline in e.g. Excel. The expression $(10^{E/S}-1)\times LOD$, or any expression linearly related to it will be called a transformed response, tR, in what follows: see Eqn. 3

$$tR \approx 10^{E/S} - 1 \qquad \text{Eqn. 3}$$

Interaction Analysis with Transformed Response Potentiometric Titration

Figure 4:
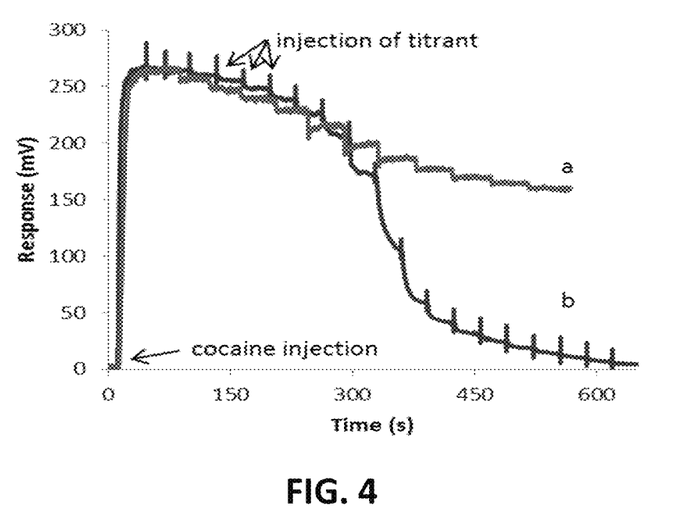
FIG. 4 shows a potentiometric titration of $10^{-5}$ M cocaine in 500 μL MES buffer 1 mM with 5 μL $10^{-4}$ M CBA (a) and TCPB (b) every 30 s.

The potentiometric titrations were used to examine the small molecule/bioparticle interactions, by measuring the potential of a working electrode in relation to the added titrant volume. Two different models were explored: one method measures the concentrations of the complexing species and the complex at the equivalence point (EP). Another method measures these concentrations at an arbitrarily chosen point largely surpassing the equivalence point (post-EP: PEP). The reason to do this, is that equivalence points are easy to localize when $K_a$ values are e.g. in the $10^{10}$ $M^{-1}$ region, but can be difficult to localize when they are in the region of molecule/bioparticle values, i.e. around $10^6$ $M^{-1}$. A "classical" titration curve (mV y-axis) is shown in FIG. 4 for the titration of cocaine with a strongly binding molecule, i.e. TCPB. As the amounts of bioparticle material available are mostly very small, the analyte volume is kept small (0.5 mL in our case) and the number and quantity of titrant additions has to be kept to a minimum. This is another restriction for locating equivalence points easily. Therefore, equivalence point determinations were done in this study with the Gran method. As we will show later in this text, changing to "Response Transformed Potentiometry Titrations" does not require exact location of equivalence points. With this method, we can work at an arbitrarily chosen point after the equivalence point (post-ep: PEP). The titration curves then will not have the classical mV ("E": see eqn. 1) y-axis but a concentration related tR (see eqn. 3) y-axis.

The study of the binding strength ($K_a$, Eqn. 3) starts with the well-known bimolecular phenomenon between an analyte (A) and a (bio)molecule or (bio)particle (M). We assume 1:1 complex formation:

$$A + M \rightleftharpoons A \cdot M \qquad \text{Eqn. 3}$$

$$K_a = \frac{[A \cdot M]}{[A][M]}$$

The dissociation constant $$\left( K_d = \frac{1}{K_a} \right)$$

and the Gibbs free energy of interaction can be calculated ($\Delta G = RT \ln K_a$) from $K_a$.

The first approach, which will be called in the text "Equivalence Point Method", uses the equivalence point of the potentiometric titration curve to determine the $K_a$. Equivalence points were obtained with the Gran method, because a small amount of titration points (less than 50) was used, and e.g. a first derivative method would be inaccurate. The Gran method is described educationally on several (internet) documents (see above), and originates in more than 60 year old publications. In the case of the titration of cocaine with CBA or TCPB (FIG. 4), the EP was determined by the Gran method. Eqn. 4 is used to calculate the association constant. $[A]_0$ is the concentration of the analyte (cocaine in this case) in the titration beaker at the start of the titration. $[A]_{EP}$ is the analyte concentration at the equivalence point. $[M]_{EP}$ is the concentration of the titrant molecule (TCPB in this case) at the equivalence point. For a 1:1 complex, $[A]_{EP}=[M]_{EP}$. $V_0$ and $V_{EP}$ are respectively the volumes in the titration beaker at the start of the titration, and at the equivalence point.

$$K_a = \frac{\frac{([A]_0 V_0 - [A]_{EP} V_{EP})}{V_{EP}}}{[A]_{EP} \cdot [M]_{EP}} = \frac{\frac{([A]_0 V_0 - [A]_{EP} V_{EP})}{V_{EP}}}{[A]_{EP}^2} \qquad \text{Eqn. 4}$$

$[A]_{EP}$ can be calculated from tR at the equivalence point (see eqn. 2), $tR_{EP}$, and from tR at the beginning of the titration, $tR_0$, as $tR_{EP}$ and $tR_0$ are linearly related to $[A]_{EP}$ and to $[A]_0$ respectively. $[A]_0$ is chosen so as to have a good compromise between sufficient sensor response (mV), and analyte concentrations which allow to reduce the quantity (the cost) of the titrant bioparticle. Using 500 µL of a $10^{-5}$ M cocaine analyte solution was a good compromise. In the future, smaller indicator electrodes (e.g. 1 mm diameter) will allow to work in more miniaturized and automated systems, which are available on the market. Working with $10^{-5}$ M analyte solutions also implies that, during titration, we will approach (or reach) the non-linear part of the potentiometric mV versus log $c_{analyte}$ calibration graph. Therefore, it is needed to work with the "Transformed Response", tR, as outlined above.

$[A]_0$ being known, we have to derive $[A]_{EP}$ via eqn. 5:

$$[A]_{EP} = [A]_0 \cdot \frac{tR_{EP}}{tR_0} = [A]_0 \left( \frac{10^{(E_{EP}/S)} - 1}{10^{(E_0/S)} - 1} \right) \qquad \text{Eqn. 5}$$

$E_0$ being the potential at the start of the titration (not to be confused with)$E^0$, i.e. at titrant volume equal to zero, and $E_{EP}$ being the potential at the equivalence point. As mentioned above, these potentials are offset to a zero value at zero analyte concentration (pure buffer solution).

The second approach, which will be called in the text "Post-EP Method", uses a point after the equivalence point of the potentiometric titration curve to determine the $K_a$. The "Post-EP Method" is used to calculate the association constant (Eqn. 6), as a function of the concentration of the analyte at the start, $[A]_0$, (which is known) and at the post-equivalence point (PEP). For the latter point we took the point at the end of the titration in the present study (Eqn. 7):

$$K_a = \frac{\frac{([A]_0 V_0 - [A]_{PEP} V_{PEP})}{V_{PEP}}}{[A]_{PEP} \left[ \frac{([M](V_{PEP} - V_0)) - \frac{([A]_0 V_0 - [A]_{PEP} V_{PEP})}{V_{PEP}}} \right]} \qquad \text{Eqn. 6}$$

-continued $$\text{with } [A]_{PEP} = [A]_0 \left( \frac{(10^{(E_{PEP}/S)} - 1)}{(10^{(E_0/S)} - 1)} \right) \qquad \text{Eqn. 7}$$

The titration of cocaine with TCPB is used as an example to explain the two different models (FIG. 4).

As shown in table 1 the obtained $K_a$ values using either the "Equivalence Point Method" (Eqn. 4) or the "Post-EP Method" (Eqn. 6) both are in the $10^9$ M$^{-1}$ range. $\Delta G°$ values are completely comparable as calculated by the two suggested methods. Similar results were obtained for potentiometric titrations of cocaine with CBA, yielding a $\Delta G$ value of 8.56±0.10 kcal mol$^{-1}$ with the EP Method and 8.00±0.13 kcal mol$^{-1}$ with the PEP Method.

Table 1: Comparison of the potentiometric titration of cocaine with TCPB between the two suggested methods based on the Equivalence Point (EP) and Post-EP (PEP). Mean values (n=amount of different electrodes tested) of $K_a$, $K_d$ and $\Delta G$ values with their corresponding standard deviations (SD) are presented.

| | Potentiometric titration of cocaine with TCPB | | | | |
|---|---|---|---|---|---|
| Method | $K_a$ (M$^{-1}$) | SD (M$^{-1}$) | $\Delta G°$ (kcal mol$^{-1}$) | SD (kcal mol$^{-1}$) | n |
| EP | 3 × 10$^9$ | 1 × 10$^9$ | 12.8 | 0.2 | 3 |
| PEP | 9 × 10$^9$ | 2 × 10$^9$ | 13.3 | 0.1 | 3 |

All the results given below are calculated with the "Post-EP Method", because the latter method is much more suited for working in biomolecular conditions. These conditions include firstly the μg availability of biocomponents at high cost, leading to small numbers of titrant injections. Secondly, the $K_a$ values of the bioparticle/small molecule complex are often in the order of $10^6$ or lower. This is at the limits of obtaining clear equivalence points in classical potentiometric titrations. In titration methods, clearly observable equivalence points are needed for quantitative determinations of analyte concentrations by addition of known concentrations of titrant. To determine $K_a$ values however, they are no prerequisite. Furthermore, if the described transformed response potentiometry titration method is used, we can work with a ligand concentration related y-axis.

Specificity of the Small Molecule/Bioparticle Complex Formation

Titration of Cocaine (as Ligand) with Different Oligonucleotides (as Titrants)

Figure 5A:
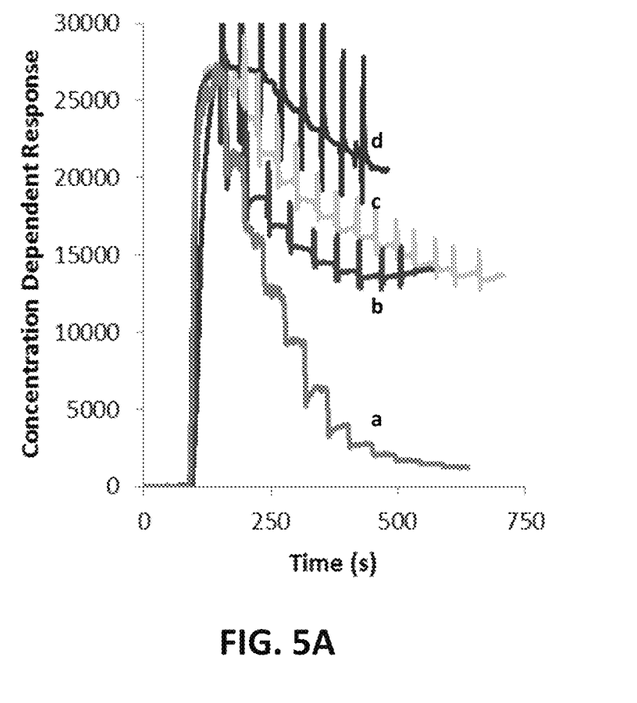
FIG. 5A illustrates potentiometric titration of cocaine with a $10^{-5}$ M cocaine in 500 μL 1 mM MES buffer with 8 μL $10^{-4}$ M CBA (curve a), CAPBA (b), 34-mer-RP (c) and 25-mer-DNA (d) every 30 s, illustrating advantages of embodiments of the present invention.

Four different oligonucleotides were used for the selectivity study. The specific selected anti-cocaine aptamer (CBA) was compared with an anti-chloramphenicol aptamer (CAPBA) and with two randomly chosen oligonucleotides (25-mer-DNA and 43-mer-RP). FIG. 5A shows the potentiometric titration of cocaine with CBA (a), CAPBA (b), 43-mer-RP (c) and 25-mer-DNA (d). This time, the concentration related transformed response, tR, is plot on the y-axis. As can be seen, the titration curve of cocaine with CBA almost completely goes back to the baseline in comparison to other oligonucleotides, visually indicating stronger binding. This type of plot allows visual indication of the binding strength, which is clearly in the order CBA>CAPBA>34-mer-RP>25-mer-DNA.

That means that CBA has a better interaction with cocaine because of the specificity of the selected bioparticle. Because the sequence of CBA had 43 bases, the 43-mer-RP was chosen for the investigation of the diagnostic performance. In the series of titrants, the CAPBA is the second, the 43-mer-RP is the third and 25-mer-DNA is the last one. Therefore, 25-mer-DNA and 43-mer-RP have little or no specific interaction with cocaine. This illustrates that the synthesized aptamer for cocaine has good recognition properties for its target, as shown by Hilton et al.

Figure 5B:
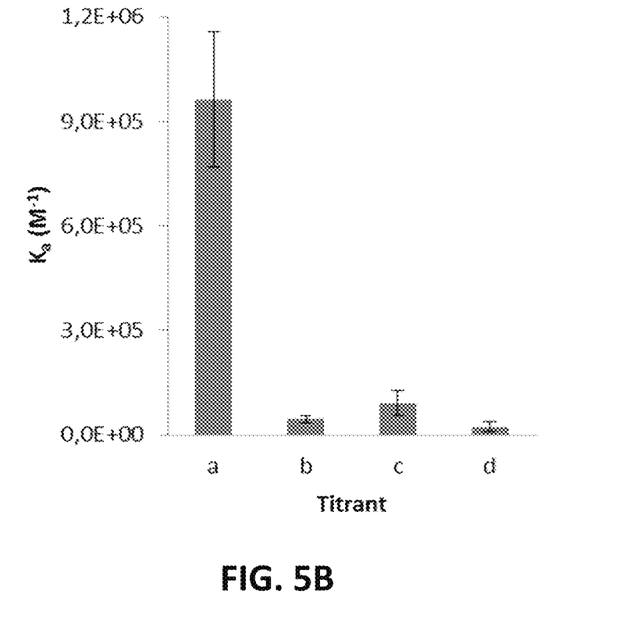
FIG. 5B illustrates association constants ($K_a$) of cocaine with CBA (a), CAPBA (b), 34-mer-RP (c) and 25-mer-DNA (d) corresponding with FIG. 5A, whereby standard deviations are shown in the histogram (with n=6 different electrodes tested for a and n=3 for b, c, d), illustrating advantages of embodiments of the present invention.

The calculated association constants for interaction between cocaine and different titrants shown in FIG. 5B are: 960×10$^3$ M$^{-1}$ for CBA, 47×10$^3$ M$^{-1}$ for CAPBA, 93×10$^3$ M$^{-1}$ for the 43-mer-RP and 24×10$^3$ M$^{-1}$ for the 25-mer-DNA, respectively. The calculated $K_d$ for CBA in our approach (1.1±0.3)×10$^{-6}$ M (n=6, n is the number of different electrodes tested) is in good agreement with the reported value for $K_d$ (between 0.4 and 10 μM) in the paper describing the synthesis of this CBA. These $K_a$ values correspond with a $\Delta G$ of 8.0±0.1 kcal mol$^{-1}$(n=6). This is a promising point, showing that we can use this new potentiometric titration approach for fast evaluation of newly synthesized aptamers, accurately and at low-cost.

Titration of Cocaine with Different Bioparticles

Figure 6A:
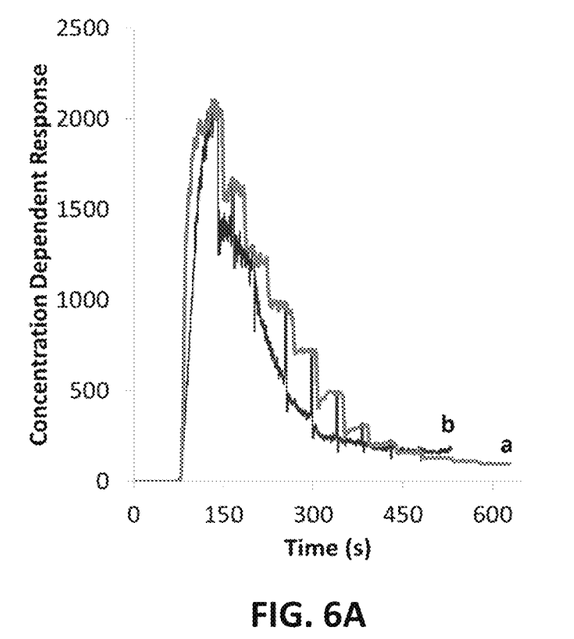
FIG. 6A shows potentiometric titration of cocaine in MES buffer with CBA (curve a) and antibody (b), injection every 30 s, illustrating advantages of embodiments of the present invention.
Figure 6B:
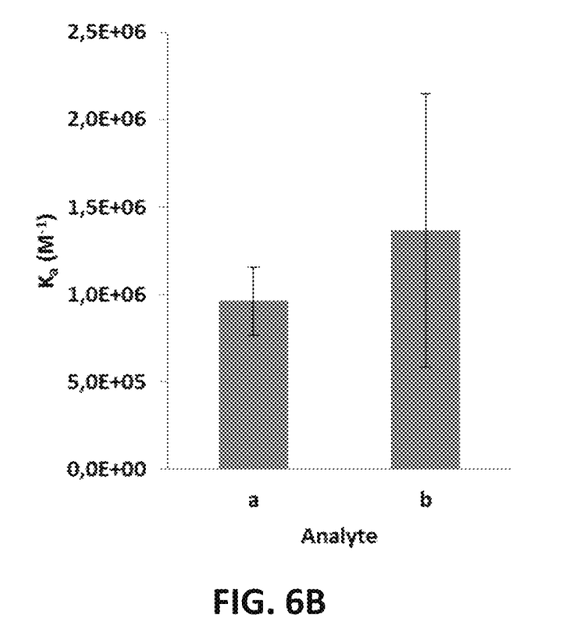
FIG. 6B shows association constants ($K_a$) of cocaine with CBA (a) and antibody (b), illustrating advantages of embodiments of the present invention, wherein standard deviations are shown in the histogram with n=6 different electrodes for a and n=3 for b.

In order to validate the suggested model for potentiometric titrations, cocaine was also titrated with another type of recognition element, i.e. an anti-cocaine antibody. FIG. 6A depicts the response transformed potentiometry titration curve of cocaine with CBA (a) and with this antibody (b). As can be seen, the curve a is almost similar to curve b. The calculated association constant for CBA, (1.0±0.2)×10$^6$ M$^{-1}$, is comparable to the value obtained for the anti-cocaine antibody, (1.4±0.8)×10$^6$ M$^{-1}$, which results in similar $\Delta G$ values for CBA, 8.0±0.1 kcal mol$^{-1}$(n=6), and anti-cocaine antibody, 8.1±0.4 kcal mol$^{-1}$(n=3). The corresponding histogram of $K_a$ values is shown in FIG. 6B.

Titration of Different Ligands with CBA (as Biomolecular Titrant)

Figure 7A:
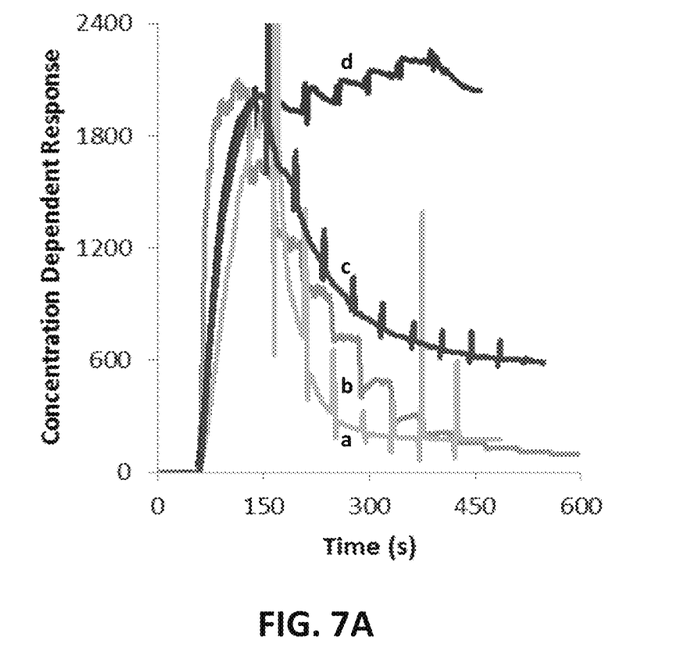
FIG. 7A illustrates Potentiometric titration of $10^{-5}$ M cocaine (a), metergoline (b), bromhexine (c) and lidocaine (d) in 500 μL 1 mM MES buffer with 8 μL $10^{-4}$ M CBA every 30 s, illustrating advantages of embodiments of the present invention.
Figure 7B:
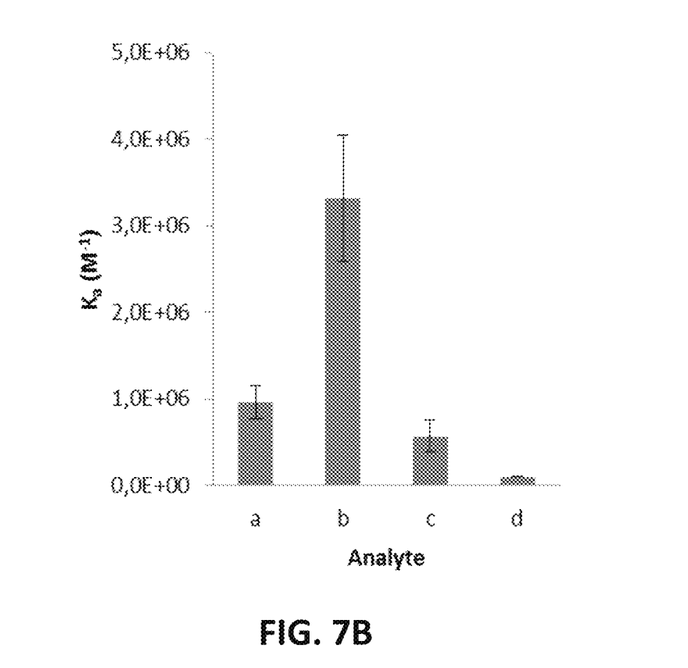
FIG. 7B shows association constants ($K_a$) of cocaine (a), metergoline (b), bromhexine (c) and lidocaine (d) with CBA illustrating advantages of embodiments of the present invention, wherein standard deviations are shown in the histogram with n=6 electrodes for a, n=4 for c, n=3 for b and d.

For studying the cross-reactivity of the specific biomolecular interaction, positively charged molecules (in MES buffer solution pH 7) were titrated with CBA. FIG. 7A illustrates the titration curve of cocaine (a), metergoline (b), bromhexine (c) and lidocaine (d) with CBA as the titrant. The calculated $K_a$ values are 960×10$^3$ M$^{-1}$, 3300×10$^3$ M$^{-1}$, 570×10$^3$ M$^{-1}$ and 100×10$^3$ M$^{-1}$, respectively. FIG. 7B shows the histogram of the $K_a$ values. The selected aptamer has better interaction with metergoline than with cocaine. Little is known on the cross-reactivity in the publishing papers for this anti-cocaine aptamer. A strong point shown in the present exemplary embodiment is that such cross-reactivities can be studied much faster than with the available methods.

The invention claimed is:

1. A method for obtaining an interaction property between a molecule or biomolecule or particle or bioparticle or a nano- or microparticle and a target particle, the method comprising:

performing a potentiometric titration for obtaining potentiometric titration results for a potentiometric measurement during titration of a solution with a titrant, the obtaining potentiometric titration results including obtaining a potential of a potentiometric indicator electrode in relation to an added titrant volume and transmitting the potential to a processor;

said solution being a solution of one of a ligand of the target particle or said molecule or biomolecule or particle or bioparticle or nano- or microparticle;

said titrant comprising the other of said target particle ligand or said molecule or biomolecule or particle or bioparticle or nano- or microparticle;

the processor transforming the obtained potential to a concentration related value; and the processor deriving based on said potentiometric titration results an interaction property between said molecule or biomolecule or particle or bioparticle or nano- or microparticle and said target particle;

wherein said transforming comprises transforming the obtained potential into the concentration related value by expressing the concentration related value as $tR \propto 10^{E/S} - 1$ wherein tR is the transformed response, E is the obtained potential and S corresponds with $(RT/zF)$ with zF the charge per mole of analyte present in the potential-forming process, R the molar gas constant and T the temperature (in Kelvin);

wherein said deriving an interaction property comprises deriving the interaction property using said concentration related value;

wherein said potentiometric measurement is performed using the potentiometric indicator electrode and a reference electrode; and wherein said transforming is performed over a concentration interval including concentration where the relation between the obtained potential and the logarithm of the concentration of the target particle is not linear.

2. The method according to claim 1, wherein the potentiometric titration results are obtained at the equivalence point of the potentiometric titration.

3. The method according to claim 1, wherein the equivalence point is obtained using a Gran method.

4. The method according to claim 1, wherein the potentiometric titration results are obtained beyond an equivalence point.

5. The method according to claim 1, wherein said interaction property is any of binding strength $K_a$, dissociation constant $K_d$ or Gibbs free energy $\Delta G$ of interaction between the molecule or biomolecule or particle or bioparticle or nano- or microparticle and the target particle.

6. The method according to claim 1, wherein the method comprises, for deriving said interaction property, visualizing a titration curve as the concentration related value as a function of time and deriving therefrom the interaction property.

7. The method according to claim 5, wherein said interaction property is the binding strength $K_a$, the binding strength $K_a$ having a value in the order of $10^6$ $M^{-1}$.

8. The method according to claim 5, wherein said interaction property is the binding strength $K_a$, the binding strength $K_a$ having a value in the order of $10^6$ $M^{-1}$ or lower.

9. A method for obtaining an interaction property between a molecule or biomolecule or particle or bioparticle or a nano- or microparticle and a target particle, the method comprising:

obtaining potentiometric titration results for a potentiometric measurement during titration of a solution with a titrant, the obtaining potentiometric titration results including obtaining a potential of a potentiometric indicator electrode in relation to an added titrant volume and transmitting the potential to a processor;

said solution being a solution of one of a ligand of the target particle or said molecule or biomolecule or particle or bioparticle or nano- or microparticle;

said titrant comprising the other of said target particle ligand or said molecule or biomolecule or particle or bioparticle or nano- or microparticle;

the processor transforming the obtained potential to a concentration related value; and the processor deriving based on said potentiometric titration results an interaction property between said molecule or biomolecule or particle or bioparticle or nano- or microparticle and said target particle;

wherein said transforming comprises transforming the obtained potential into the concentration related value by expressing the concentration related value as $tR \propto 10^{E/S} - 1$ wherein tR is the transformed response, E is the obtained potential and S corresponds with (RT/zF) with zF the charge per mole of analyte present in the potential-forming process, R the molar gas constant and T the temperature (in Kelvin);

wherein said deriving an interaction property comprises deriving the interaction property using said concentration related value;

wherein said transforming is performed over a concentration interval including concentration where the relation between the obtained potential and the logarithm of the concentration of the target particle is not linear; and wherein the method comprises, for deriving said interaction property, visualizing a titration curve as the concentration related value as a function of time and deriving therefrom the interaction property.

* * * * *

SEQUENCE LISTING

<160> NUMBER OF SEQ ID NOS: 3

<210> SEQ ID NO 1
<211> LENGTH: 43

```
<212> TYPE: DNA
<213> ORGANISM: Artificial Sequence
<220> FEATURE:
<223> OTHER INFORMATION: aptamer

<400> SEQUENCE: 1
atctcgggac gacaggattt tcctcaatga agtgggtcgt ccc                    43

<210> SEQ ID NO 2
<211> LENGTH: 25
<212> TYPE: DNA
<213> ORGANISM: Artificial Sequence
<220> FEATURE:
<223> OTHER INFORMATION: oligonucleotides

<400> SEQUENCE: 2
aaaatatcat ctttggtgtt tccta                                       25

<210> SEQ ID NO 3
<211> LENGTH: 80
<212> TYPE: DNA
<213> ORGANISM: Artificial Sequence
<220> FEATURE:
<223> OTHER INFORMATION: aptamer

<400> SEQUENCE: 3
agcagcacag aggtcagatg acttcagtga gttgtcccac ggtcggcgag tcggtggtag   60
cctatgcgtg ctaccgtgaa                                              80
```